(12) United States Patent
Kreuzer

(10) Patent No.: US 10,888,469 B2
(45) Date of Patent: Jan. 12, 2021

(54) ABSORBENT ARTICLE WITH RAISABLE TOPSHEET

(71) Applicant: The Procter & Gamble Company, Cincinnati, OH (US)

(72) Inventor: Carsten Heinrich Kreuzer, Hofheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 313 days.

(21) Appl. No.: 15/984,727

(22) Filed: May 21, 2018

(65) Prior Publication Data

US 2018/0338870 A1  Nov. 29, 2018

(30) Foreign Application Priority Data

May 24, 2017 (EP) .................................. 1717288
May 24, 2017 (EP) .................................. 17172878
May 24, 2017 (EP) .................................. 17172879

(51) Int. Cl.
*A61F 13/495* (2006.01)
*A61F 13/496* (2006.01)
(Continued)

(52) U.S. Cl.
CPC .......... *A61F 13/495* (2013.01); *A61F 13/496* (2013.01); *A61F 13/49017* (2013.01);
(Continued)

(58) Field of Classification Search
CPC .......... A61F 13/49001; A61F 13/49413; A61F 13/4942; A61F 13/49466; A61F 13/49473;
(Continued)

(56) References Cited

U.S. PATENT DOCUMENTS 3,848,594 A   11/1974  Buell
3,860,003 A    1/1975  Buell
(Continued)

FOREIGN PATENT DOCUMENTS

EP       0149880 A2    7/1985
JP      H02065861 A    3/1990

OTHER PUBLICATIONS

EP Search Report for EP17172878.5-1308, dated Oct. 24, 2017 (6 pages).
(Continued)

*Primary Examiner* — Catharine L Anderson
*Assistant Examiner* — Lynne Anderson
(74) *Attorney, Agent, or Firm* — Brian M. Bolam; Andrew J. Hagerty

(57) ABSTRACT

An absorbent article for personal hygiene having a front edge and a back edge and comprising a liquid impermeable backsheet, a liquid permeable topsheet, an absorbent core and a pair of barrier leg cuffs disposed symmetrically relative to the longitudinal axis. Each barrier leg cuff is defined by a proximal edge attached to the rest of the article and an elasticized terminal edge that can protrude upwards. The topsheet comprises a raisable region that is attached to the barrier leg cuffs so that when the barrier leg cuffs are raised, the raisable region is lifted up by the barrier leg cuffs and an empty volume is formed between the raisable region and the chassis of the article underneath.

14 Claims, 6 Drawing Sheets

(51) Int. Cl.
*A61F 13/515* (2006.01)
*A61F 13/49* (2006.01)
*A61F 13/531* (2006.01)
*A61F 13/511* (2006.01)
*A61F 13/512* (2006.01)
*A61F 13/53* (2006.01)

(52) U.S. Cl.
CPC .......... *A61F 13/511* (2013.01); *A61F 13/512* (2013.01); *A61F 13/515* (2013.01); *A61F 13/51104* (2013.01); *A61F 13/531* (2013.01); *A61F 2013/4953* (2013.01); *A61F 2013/49093* (2013.01); *A61F 2013/5127* (2013.01); *A61F 2013/5315* (2013.01); *A61F 2013/530481* (2013.01)

(58) Field of Classification Search
CPC ............. A61F 13/495; A61F 13/51104; A61F 13/512; A61F 13/5126; A61F 2013/49092; A61F 2013/49093; A61F 2013/4944; A61F 2013/4948; A61F 2013/49493; A61F 2013/5127; A61F 2013/515; A61F 2013/5315; A61F 2013/532; A61F 2013/533
See application file for complete search history.

(56) References Cited

U.S. PATENT DOCUMENTS

| | | | |
|---|---|---|---|
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,609,518 A | 9/1986 | Curro et al. | |
| 4,629,643 A | 12/1986 | Curro et al. | |
| 4,662,875 A | 5/1987 | Hirotsu et al. | |
| 4,695,278 A | 9/1987 | Lawson | |
| 4,699,622 A | 10/1987 | Toussant et al. | |
| 4,710,189 A | 12/1987 | Lash | |
| 4,795,454 A | 1/1989 | Dragoo | |
| 4,808,178 A | 2/1989 | Aziz et al. | |
| 4,846,815 A | 7/1989 | Scripps | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,006,394 A | 4/1991 | Baird | |
| 5,137,537 A | 8/1992 | Herron et al. | |
| 5,151,092 A | 8/1992 | Buell et al. | |
| 5,221,274 A | 6/1993 | Buell et al. | |
| 5,242,436 A | 9/1993 | Weil et al. | |
| 5,499,978 A | 3/1996 | Buell et al. | |
| 5,549,791 A | 8/1996 | Herron et al. | |
| 5,591,152 A | 1/1997 | Buell et al. | |
| 5,607,760 A | 3/1997 | Roe | |
| 5,609,587 A | 3/1997 | Roe | |
| 5,643,588 A | 7/1997 | Roe et al. | |
| H001732 H | 6/1998 | Johnson | |
| 5,814,570 A | 9/1998 | Cohen | |
| 5,837,352 A | 11/1998 | English et al. | |
| 5,843,056 A | 12/1998 | Good et al. | |
| 5,968,025 A | 10/1999 | Roe et al. | |
| 6,169,225 B1* | 1/2001 | Otsubo | A61F 13/42 604/361 |
| 6,336,922 B1 | 1/2002 | VanGompel et al. | |
| 6,432,098 B1 | 8/2002 | Kline et al. | |
| 6,482,191 B1 | 11/2002 | Roe et al. | |
| 6,632,504 B1 | 10/2003 | Gillespie et al. | |
| 6,645,569 B2 | 11/2003 | Cramer et al. | |
| 6,716,441 B1 | 4/2004 | Osborne et al. | |
| 6,730,387 B2 | 5/2004 | Rezai et al. | |
| 6,786,895 B1 | 9/2004 | Schmitz | |
| 6,863,933 B2 | 3/2005 | Cramer et al. | |
| 7,112,621 B2 | 9/2006 | Rohrbaugh et al. | |
| 7,361,167 B2* | 4/2008 | Erickson | A61F 13/15747 604/385.01 |
| 7,524,312 B2* | 4/2009 | Onishi | A61F 13/49426 604/385.101 |
| 7,563,257 B2 | 7/2009 | Nakajima et al. | |
| 7,654,990 B2* | 2/2010 | Nakajima | A61F 13/495 604/385.101 |
| 7,666,173 B2* | 2/2010 | Mishima | A61F 13/4915 604/385.101 |
| 7,744,576 B2 | 6/2010 | Busam et al. | |
| 7,785,310 B2* | 8/2010 | Sakano | A61F 13/4942 604/378 |
| 7,786,341 B2 | 8/2010 | Schneider et al. | |
| 8,206,533 B2 | 6/2012 | Hundorf et al. | |
| 8,236,715 B2 | 8/2012 | Schmidt et al. | |
| 8,491,558 B2 | 7/2013 | Roe et al. | |
| 8,502,012 B2 | 8/2013 | Meyer et al. | |
| 8,568,566 B2 | 10/2013 | Jackels et al. | |
| 8,581,019 B2 | 11/2013 | Carlucci et al. | |
| 8,680,362 B2 | 3/2014 | McKiernan et al. | |
| 9,000,254 B2 | 4/2015 | McGregor et al. | |
| 9,066,838 B2 | 6/2015 | Hippe et al. | |
| 9,072,634 B2 | 7/2015 | Hundorf et al. | |
| 9,211,618 B2 | 12/2015 | Hethcock et al. | |
| 9,273,419 B2 | 3/2016 | Flohr et al. | |
| 9,358,161 B2 | 6/2016 | Lawson et al. | |
| 9,474,657 B2 | 10/2016 | Berrizbeitia et al. | |
| 9,474,660 B2 | 10/2016 | Kirby et al. | |
| 9,480,609 B2 | 11/2016 | Kirby et al. | |
| 9,484,294 B2 | 11/2016 | Yoneda et al. | |
| 9,750,651 B2 | 9/2017 | Bianchi et al. | |
| 9,789,009 B2 | 10/2017 | Joseph | |
| 9,789,011 B2 | 10/2017 | Roe et al. | |
| 2002/0151861 A1* | 10/2002 | Klemp | A61F 13/511 604/385.19 |
| 2003/0105190 A1 | 6/2003 | Diehl et al. | |
| 2003/0148684 A1 | 8/2003 | Cramer et al. | |
| 2005/0008639 A1 | 1/2005 | Cramer et al. | |
| 2005/0080821 A1 | 4/2005 | Breil et al. | |
| 2007/0093767 A1 | 4/2007 | Carlucci et al. | |
| 2008/0312622 A1 | 12/2008 | Hundorf et al. | |
| 2009/0318884 A1 | 12/2009 | Meyer et al. | |
| 2011/0268932 A1 | 11/2011 | Catalan et al. | |
| 2012/0330263 A1 | 12/2012 | Lawson et al. | |
| 2013/0203678 A1 | 8/2013 | Francois et al. | |
| 2014/0005622 A1 | 1/2014 | Wirtz et al. | |
| 2014/0039434 A1 | 2/2014 | Xu et al. | |
| 2014/0039438 A1 | 2/2014 | Ferrer et al. | |
| 2014/0121625 A1 | 5/2014 | Kirby et al. | |
| 2014/0163501 A1 | 6/2014 | Ehrnsperger et al. | |
| 2015/0045759 A1 | 2/2015 | Martynus et al. | |
| 2015/0065973 A1* | 3/2015 | Roe | A61F 13/5125 604/361 |
| 2015/0223995 A1 | 8/2015 | Martynus et al. | |
| 2015/0230997 A1* | 8/2015 | Suzuki | A61F 13/4942 604/385.28 |
| 2015/0250662 A1 | 9/2015 | Isele et al. | |
| 2015/0282998 A1 | 10/2015 | Arizti et al. | |
| 2015/0342796 A1 | 12/2015 | Bianchi et al. | |
| 2016/0235594 A1 | 8/2016 | Ehrnsperger et al. | |
| 2016/0235603 A1 | 8/2016 | Ehrnsperger et al. | |
| 2016/0235604 A1 | 8/2016 | Ehrnsperger et al. | |
| 2016/0270971 A1 | 9/2016 | Raycheck et al. | |
| 2016/0270974 A1 | 9/2016 | Surushe et al. | |
| 2016/0341653 A1 | 11/2016 | Molas et al. | |
| 2017/0135870 A1 | 5/2017 | Kamphus | |

OTHER PUBLICATIONS

Search Report for EP17172879.3-1308, dated Sep. 20, 2017 (6 pages).
PCT International Search Report, dated Jul. 10, 2018 (15 pages).

* cited by examiner

ABSORBENT ARTICLE WITH RAISABLE TOPSHEET

CROSS REFERENCE TO RELATED APPLICATIONS

This application claims priority to EP Application No. 17172878.5, filed May 24, 2017, and to EP Application No. 17172879.3, filed May 24, 2017, and to EP Application No. 17172881.9, filed May 24, 2017, the substances of which are incorporated herein by reference.

FIELD OF THE INVENTION

The invention is directed to personal hygiene absorbent articles worn in the crotch region of the wearer, for example a baby diaper or an adult incontinence product. The article comprises a pair of elasticized barrier leg cuffs each defined by a proximal edge attached to the rest of the article and a distal edge that protrudes upwards from the chassis of the article when worn by the wearer. The article further comprises a topsheet on its wearer-facing side, the topsheet having a raisable region attached to the barrier leg cuffs away from the proximal edge. When the barrier cuffs are protruding upwards, the raisable region is lifted away from the chassis of the article underneath by the cuffs and an empty volume is formed between the raisable region and the rest of the article underneath.

BACKGROUND OF THE INVENTION

Absorbent articles for personal hygiene are designed to absorb and contain body exudates, in particular urine and feces. These absorbent articles typically comprise several layers that provide different functions. The wearer-facing side of the article comprises a topsheet that should be capable of quickly acquiring fluid and feel soft to the skin. The garment-facing side comprises or consists of a backsheet which protects the wearer's clothes or linens. Absorbent articles further comprise an absorbent core between these two layers for retaining the exudates. It is also known to provide one or more acquisition and distribution layers between the topsheet and the absorbent core. These intermediate layers are designed to quickly acquire and distribute the fluid away from the topsheet and direct the fluid into the absorbent core for storage.

It is desirable to keep away excrements, in particular runny feces, from the skin of the wearer to improve the wearer comfort and the skin's hygiene. It is also desirable to limit topsheet runoff which can occur when several gushes of liquid come in quick successions and saturate the absorbent system including the acquisition/distribution layers. Articles have been proposed comprising a void space in the absorbent core, a so-called pocket, to receive feces. However this part of the absorbent core does not comprise absorbent material, which may be detrimental for the overall absorbency of the article. Furthermore, these pockets may be difficult to make. Another solution is suggested in JP patent application JPH02-65861 (Katayama) which discloses a diaper having a surface sheet having a plurality of holes and partially attached to elasticized barrier leg cuffs so that the surface sheet is lifted by the barrier leg cuffs when these are in a protrusion state. This creates a buffer space for loose stools between the surface sheet and the rest of the article.

While the known absorbent articles can have good overall properties, there is a continuous need to improve comfort, fit and efficiency of the current articles. The present invention addresses these problems.

SUMMARY OF THE INVENTION

The invention is directed to an absorbent article for personal hygiene having a front edge and a back edge notionally defining a longitudinal axis extending from the middle of the front edge to the middle of the back edge, the absorbent article comprising:
  a wearer-facing side comprising a liquid permeable topsheet;
  a garment-facing side comprising a liquid impermeable backsheet;
  an absorbent core between the topsheet and the backsheet and the absorbent core comprising an absorbent material,
  a chassis comprising the absorbent core and the backsheet;
  a pair of barrier leg cuffs disposed symmetrically relative to the longitudinal axis, each barrier leg cuff defined by a proximal edge attached to the chassis of the article, and an elasticized terminal edge that can be raised away from the chassis.

The topsheet comprises a raisable region attached to the barrier leg cuffs at a position away from the proximal edges of the barrier leg cuffs, so that when the barrier leg cuffs are raised away from the chassis, the raisable region is lifted up by the barrier leg cuffs and an empty volume is formed between the raisable region and the chassis of the article.

In an aspect of the invention, the length of the wearer-facing side of the article is shorter than the length of the garment-facing side of the article, as measured along the longitudinal axis. In this way, the garment-facing side of the article, in particular the backsheet and any layers attached to the backsheet, can more easily curve outwardly and this facilitates the expansion of the empty volume formed between the raisable region and the chassis. This empty volume is useful to store away from the skin of the user semi-solid and solid excrements. The empty volume also forms a larger temporary storage for urine which is kept away from the skin of the wearer until it is acquired or absorbed by the inner layers of the article.

In another aspect, the absorbent core comprises at least one, and preferably at least a pair, of channel areas. The channel areas improve the flexibility of the article by providing axes of flexibility In another aspect, the article further comprises a front waist cap and/or a back waist cap. The front waist cap extends inwardly from the front edge of the article and has an inward-looking edge. The back waist cap extends inwardly from the back edge of the article and has an inward-looking edge. The front side of the raisable region of the topsheet is attached to the front waist cap at a position intermediate the front edge of the article and the inward-looking edge of the front waist cap, and/or the back side of the raisable region of the topsheet is attached to the back waist cap at a position intermediate the back edge of the article and the inward-looking edge of the back waist cap. A portion of the front waist cap and/or the back waist cap comprising the inward-looking edge(s) are raised simultaneously with the raisable portion of the topsheet. The inward-looking edge of the front waist cap and/or the back waist cap may comprise a recess. The recess may take different form, in particular a concave curve in the middle of the inward-looking edge.

The different aspects may be used individually or combined in an absorbent article according to the invention.

The absorbent articles of the invention will be further illustrated in the below description and in the Figures in the form of a taped diaper. For ease of discussion, the absorbent article and its components will be discussed with reference to the numerals referred to in these Figures, however nothing in this description should be considered limiting the scope of the claims unless explicitly indicated otherwise. In particular, the invention may also be used in pant type diaper, which are pre-formed and are worn like an underwear garment.

DETAILED DESCRIPTION OF THE INVENTION

General Description of the Absorbent Article

As used herein, the term "absorbent article for personal hygiene" refers to disposable devices which are placed against or in proximity to the crotch of a wearer to absorb and contain exudates discharged from the body. An exemplary absorbent article according to the invention in the form of a baby taped diaper 20 is represented in FIGS. 1-5. This diaper 20 is shown for illustration purpose only, as the invention may be used for making a wide variety of diapers or other absorbent articles such as diaper pants, adult incontinence pants or feminine sanitary pads. The present invention may nevertheless be especially useful for diapers for new born babies aged less than 1 year, in particular less than 6 months, as these babies may have especially runny or pasty stools that can be acquired in the volume formed under the raisable region of the topsheet. The absorbent core comprising the channel areas 26 with optional channel bonds 27 is illustrated separately in FIGS. 6-7 for readability.

Figure 1:
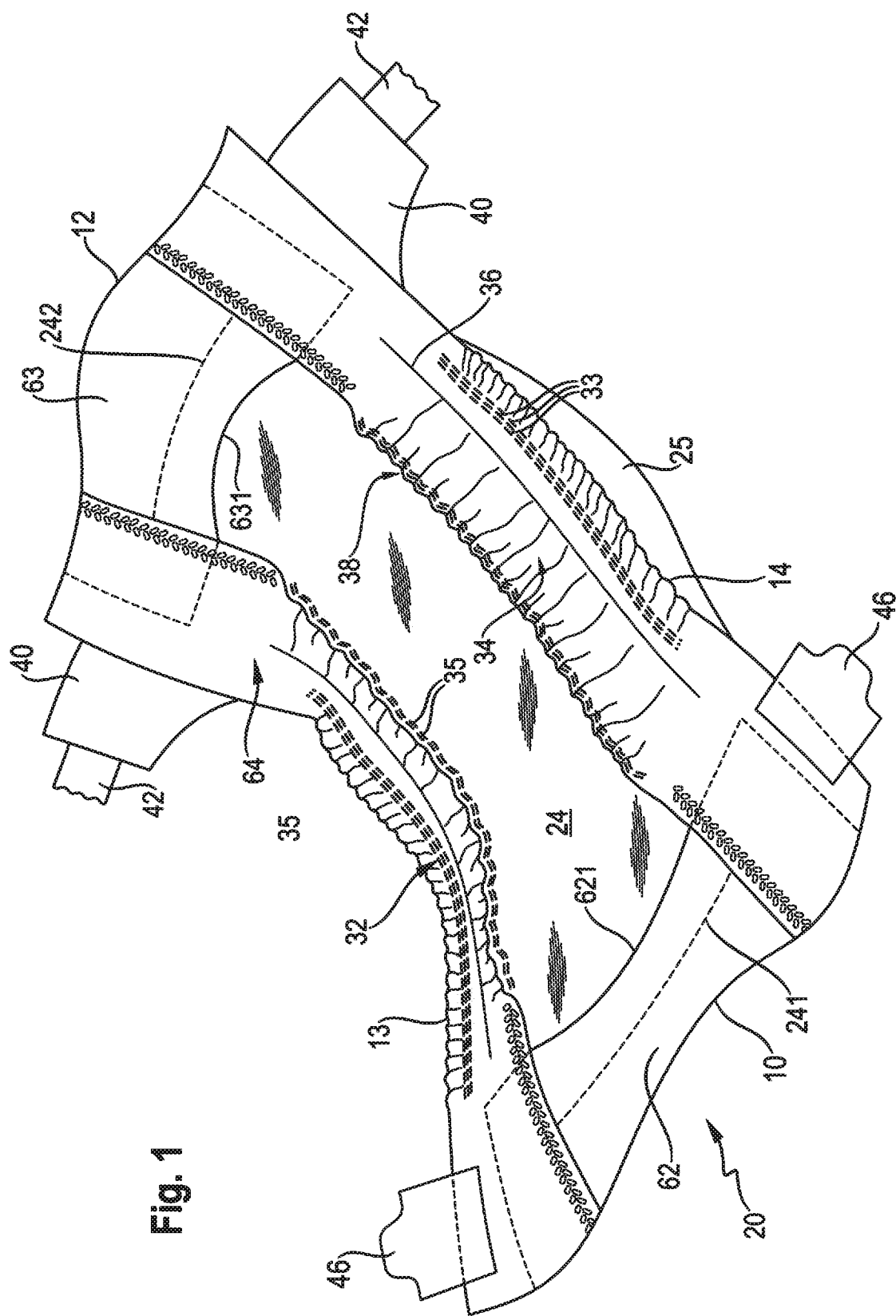
FIG. 1 is a perspective view of an exemplary article of the invention in the form of a taped diaper.

FIG. 1 shows a perspective view of the taped diaper in an open configuration. As indicated, this representation of a taped diaper is not limiting, the invention is also applicable to diaper pants which have pre-sealed side seams. The absorbent article 20 comprises a front edge 10, a back edge 12, and two longitudinally-extending side (lateral) edges 13, 14. The front edge 10 is the edge of the article which is intended to be placed towards the front of the wearer when worn, and the back edge 12 is the opposite edge. The front edge 10 and the back edge 12 of the diaper can be releasably attached together using the fastening tabs 42 and a landing zone 44 (not shown on FIG. 1) to form the closed article as is known in the art. The closed article comprises a waist opening formed by the front edge 10 and back edge 12, and two leg openings formed by the lateral edges of the diaper 13, 14.

Figure 3:
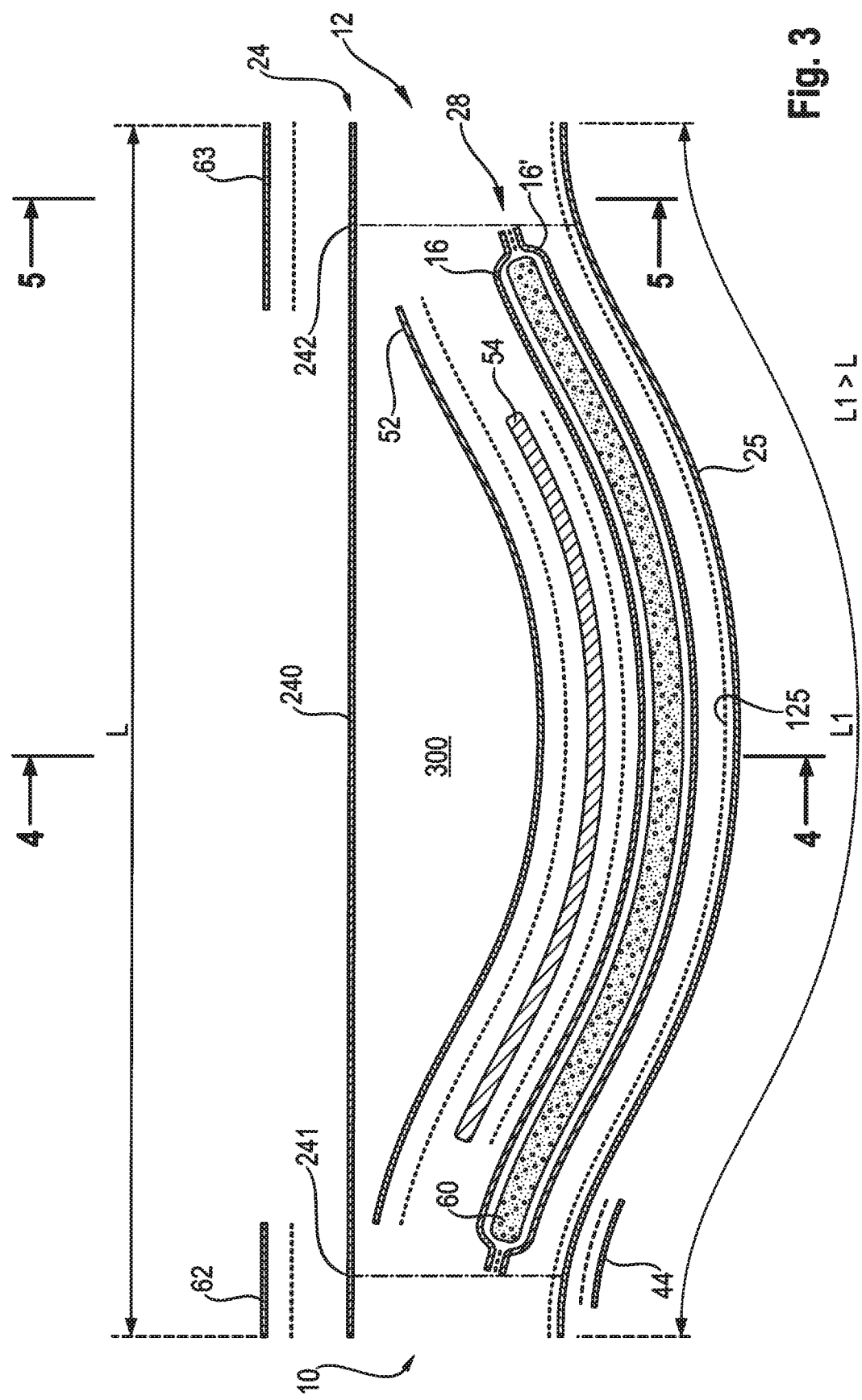
FIG. 3 shows a schematic cross-section of the diaper of FIG. 2 in the longitudinal direction.
Figure 4:
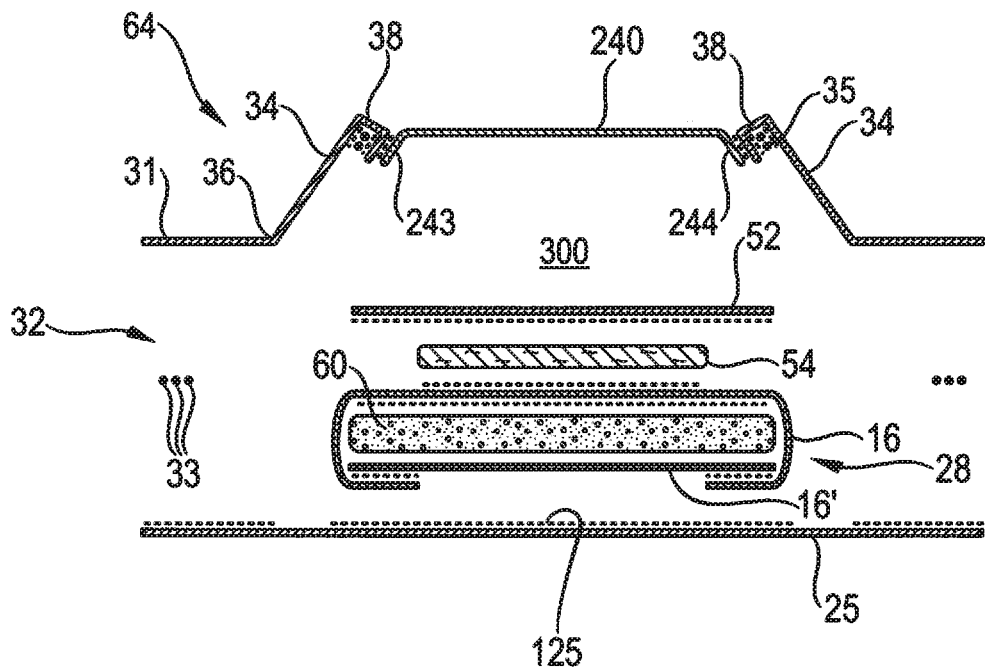
FIG. 4 shows a schematic cross-section of the diaper in the transversal direction viewed from the middle of the article.
Figure 5:
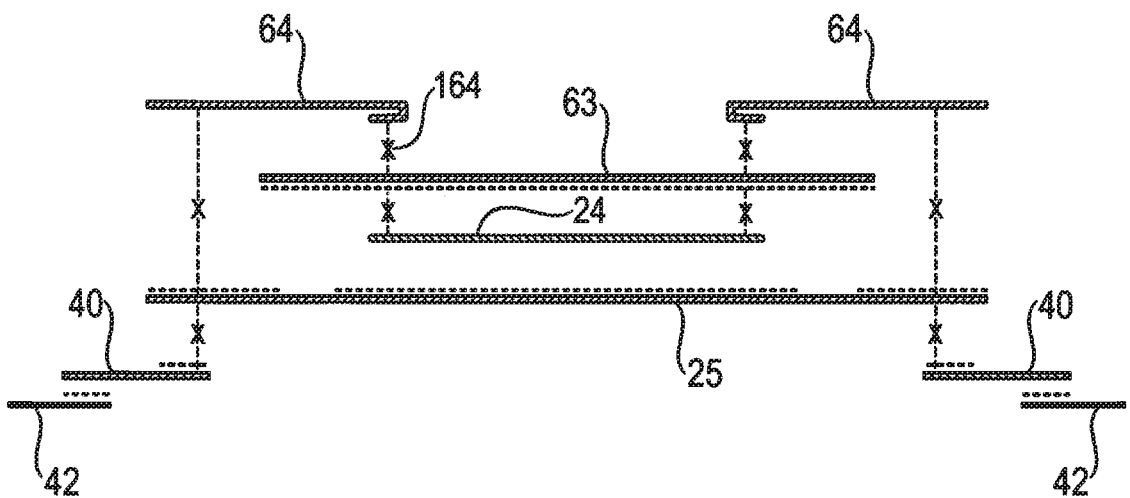
FIG. 5 shows a schematic cross-section of the diaper in the transversal direction viewed in the back region of the article.

The absorbent article 20 comprises a liquid permeable topsheet 24 on its wearer-facing side, a liquid impermeable backsheet 25 on the opposite, garment-facing side, and an absorbent core 28 between the topsheet and the backsheet, as better seen in the cross-section views of FIGS. 3-5. The chassis of the article is referred herein as the backsheet and the absorbent core, considered individually and collectively, as well as any other layers which are attached to these layers directly or indirectly so that they remain in the same spatial configuration relative to these layers during use. The backsheet and the absorbent core may be uniformly attached to each over the whole of their overlapping surface, or more commonly in a core-to-backsheet gluing pattern that may comprise longitudinally extending adhesive stripes, as is known in the art. The absorbent core 28 may typically comprise a core wrap 16, 16' enclosing an absorbent material 60, as will be detailed further below. The absorbent core may optionally comprise longitudinally elongated absorbent material-free channels 26, as will be discussed in more details with reference to FIGS. 6-7. The absorbent article may comprise an acquisition layer 52 and/or a distribution layer 54 between the topsheet and absorbent core. Examples of these optional layers will be provided further below.

The article may advantageously also comprise a front waist cap 62 and/or a back waist cap 63 disposed adjacent the front edge and back edge of the article respectively and extending inwardly towards the center of the article up to their inward-looking edge 621, 632. If the term "waist caps" is used herein without further qualification, it refers to the front waist cap and/or the back waist cap, collectively and individually. The waist caps are partially raisable with the topsheet and have barrier properties. The waist caps help containing the excrements collected in the volume formed under the raisable region topsheet and thus prevent these from leaking through the waist opening of the diaper. The inward-looking edge of the waist caps is not straight but present a recess, which may be a curve-shaped and centered on the longitudinal axis of the article in order to reduce possible interference with the topsheet in the middle of the article while still providing a barrier effect along the front and back lateral sides of the article.

The article further comprises a pair of barrier leg cuffs 34, each cuff having a proximal edge 36 attached to the chassis of the article and a raisable, elasticized, distal edge 38, as better seen on FIG. 4. Each barrier leg cuff 34 may be formed by a cuff material 64, which is typically a nonwoven, and an elastic component 35 disposed at the distal edge 38 of the barrier leg cuff. A "nonwoven web" or more simply a "nonwoven" is defined as an "engineered fibrous assembly which has been given a designed level of structural integrity by physical and/or chemical means with the exclusion of paper, woven or knitted materials". The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. Nonwovens may also be multilayer webs, in particular comprising spunbond (S) and meltblown (M) layers, such as SM, SMS, SMMS multilayer etc. as is known in the art. The basis weight of nonwoven is usually expressed in grams per square meter ($g/m^2$ or gsm).

The elastic components 35 at the distal edges can typically comprise one or more elastic strands extending along the length of the distal edges of the barrier leg cuffs 34. When the article is put on the wearer, these elastic strands exert a contracting force on the barrier leg cuffs, which drives the barrier leg cuffs to assume an upstanding position relative to the chassis of the absorbent article, which is the absorbent core, the backsheet and the other layers attached congruently with these layers. Other optional layers that can be attached to and form part of the chassis include an acquisition layer 52, a distribution layer 54, and the gasketing cuffs 32. Barrier leg cuffs are typically useful to maintain a good contact of the diaper at the lines of junction of the crotch and the thighs of the wearer, as is known in the art. In the present invention, a raisable region 240 of the topsheet 24 is attached to the barrier leg cuffs at a position away from the proximal edges, in particular at or close to the distal edges 38 of the barrier cuffs. It is however not excluded that the topsheet may be attached to any intermediate position between the distal and the proximal edges of the barrier leg cuffs. This region of the topsheet is at least partially unattached to the chassis of the diaper, so that it forms a raisable region 240 of the topsheet that can be lifted upwards and away from the rest of the article (typically the chassis) by the barrier leg cuffs when the article is worn by the user. The garment-facing side of the article may advantageously have a length L1 in the longitudinal direction with is longer than the length L of the wearer-facing side of the article, as illustrated in FIG. 3. This difference of length helps forming the empty volume for receiving the excrements under the raisable region of the topsheet of the article.

The article may also comprise a pair of gasketing cuffs 32 which may be formed by elastic components such as elastic strands 33 disposed between the backsheet 25 and a cuff material 31, which is typically made from an extension of the same cuff material 64 used for the barrier leg cuffs 32.

Figure 2:
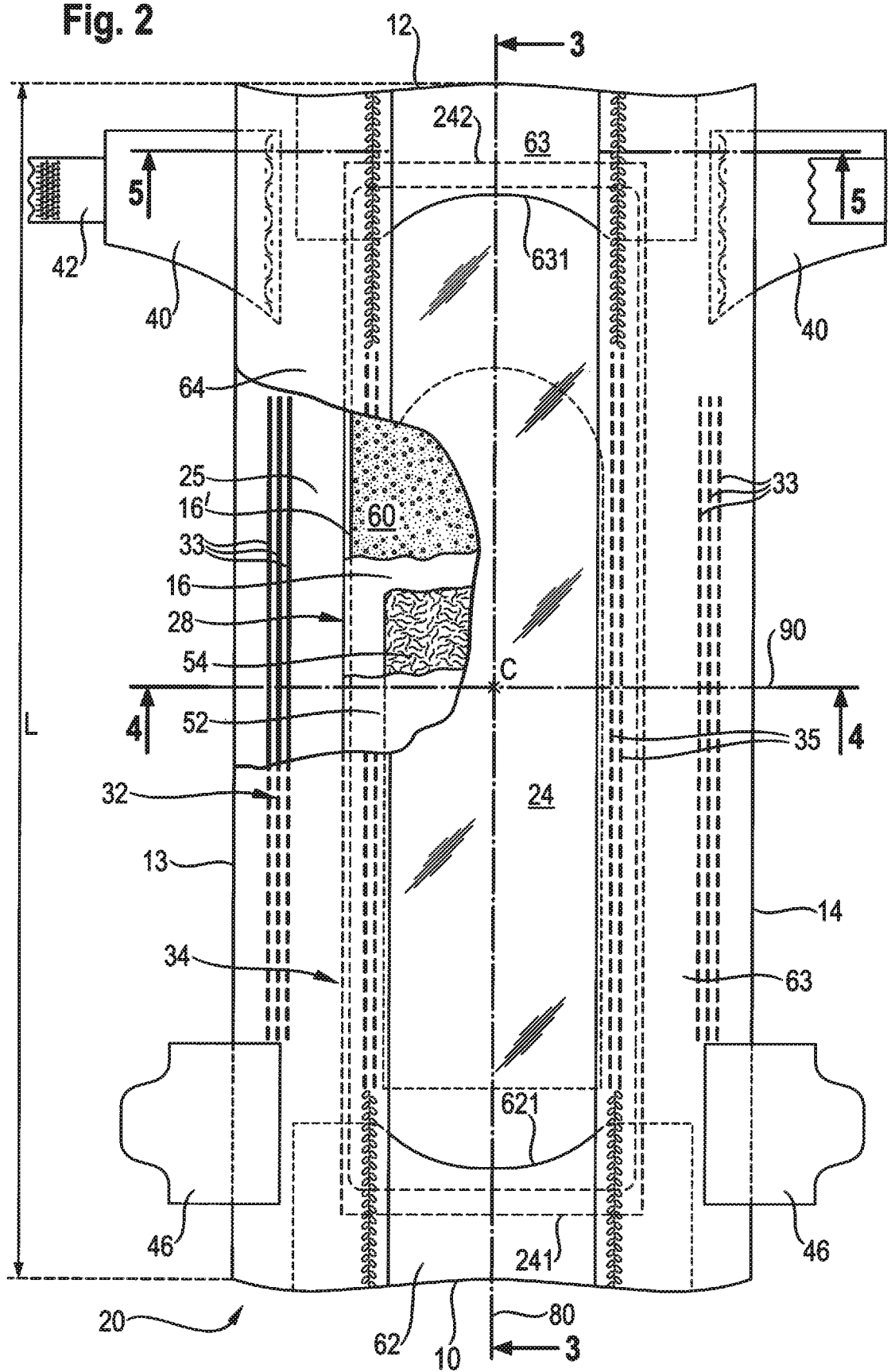
FIG. 2 is a top side view of the wearer-facing side of the diaper pulled taut, with some of the inner layers of the article partially exposed.

FIG. 2 shows the article of FIG. 1 from the wearer-facing side in a flattened configuration. The article may be typically held flat using clamps along the periphery of the article and/or a sticky surface despite the presence of elasticized components. As shown in the Figure, the absorbent article can be notionally divided by a longitudinal axis 80 extending along a longitudinal direction from the middle of the front edge 10 to the middle of the back edge 12 of the article and dividing the article in two substantially symmetrical halves relative to this axis. Closed articles such as training pants or adult incontinent pants may be cut open along the side seams to apply them on a flat surface. When the garment-facing side of the article is longer than its wearer-facing side, the backsheet and more generally the chassis of the article may be wrinkled when the wearer-facing side is pulled taut on a flat surface as shown on FIG. 2. These wrinkles on the opposite side than the topsheet are not represented in FIG. 2. Unless otherwise indicated, dimensions and areas disclosed herein apply to the article in this flat-out configuration. The wearer-facing side of the article has a length L as measured along the longitudinal axis 80 from the front edge 10 to the back edge 12 of the article. The topsheet may typically extend along the whole length L of the article, with the front and back waist caps covering the topsheet at the position adjacent the front and back edges of the article. But it is also not excluded that the topsheet may be shorter that the wearer-facing side, for example the topsheet may stop at a position under the waist caps before the front and/or back edges.

In the example illustrated in the drawings, the raisable portion 240 of the topsheet corresponds almost entirely to the topsheet layer 24 apart from two terminal portions of the topsheet which are attached to the backsheet 25 towards the front edge 10 of the article along the line 241 and the back edge 12 along the line 242 respectively.

FIG. 2 shows that the absorbent article can also be notionally divided by a transversal axis 90 into a front region and a back region of equal length of half L, as measured on the longitudinal axis. The transversal axis 90 is perpendicular to the longitudinal axis 80 and placed at half the length of the article as seen on the wearer-facing side. The intersection of the longitudinal axis 80 and the transversal axis 90 is defined herein as the centerpoint C of the article. The barrier leg cuffs 34 extend longitudinally at least partially between the front edge and the back edge of the absorbent article on opposite sides of the longitudinal axis and are at least present at the level of the center point C of the article.

FIG. 3 shows a longitudinal cross-section of the absorbent article. The wearer-facing side of the article has a length L, which is measured with the article pulled taut as in FIG. 2 to remove any wrinkles in the wearer-facing side but without additional tension so as not to deform the article more than necessary for the measurement. The wearer-facing side may typically have the same length as the topsheet 24, as illustrated in FIG. 3, but it is not excluded that the topsheet may be shorter for example if the topsheet does not extend completely under the waist caps 62, 63. The garment-facing side of the article has a length L1 may be the same or advantageously longer as L. The length L1 may be measured by stretching the article taut under the same condition as for the measurement of L, that is by pulling the garment-facing side just enough to remove the wrinkles, and measuring the length of the garment-facing side. Typically, the garment-facing side will be formed by the backsheet and will have the same length as the backsheet. Thus, the backsheet may also be removed from the rest of the article to measure its length, if desired. The length L1 may in particular range from 101% to 140% of the length L, in particular from 105% to 130% of the length L.

FIGS. 3-5 also show how the different layers of the absorbent article may be attached to another. Dotted lines between two layers illustrate an attachment, in particular an adhesive applied on one of the layer. Adhesive attachments may be made by any conventional adhesive means such as slot glue application, spiral application, etc. It is also not excluded that other attachment means may be used, such a pressure and heat bonding, ultrasound bonding when feasible and as is known in the art. FIG. 3 illustrates more clearly the formation of an empty volume 300 between the raisable portion 240 of the topsheet 24 and the next layer attached to the chassis, in this case an acquisition layer 52. It is however not excluded that the topsheet may be a laminate of two or more layers as is known in the art, in that case the volume will be formed between the laminate and the next layer of the chassis e.g. the acquisition layer. The raisable portion 240 of the topsheet may be delimited in the longitudinal direction by a front side 241 and a back side 242. The portion of the topsheet 24 extending beyond the front side 241 of its raisable portion may be attached to the chassis, e.g. as represented by adhesively attaching it to the backsheet up to the front edge 10 of the article. Likewise, the portion of the topsheet 24 extending beyond the back side 242 of its raisable portion may be attached to the chassis, e.g. as represented by adhesively attaching it to the backsheet up to the back edge 12 of the article. A front waist cap 62 and back waist cap 63 may be attached on top of the topsheet towards the front and back edges respectively.

FIG. 4 shows a cross-section of the article along its transversal centerline 90, illustrating how the raisable portion 240 of the topsheet may be bonded along its two longitudinally-extending sides 243, 244 to each distal edge 38 of the barrier leg cuffs 34. The topsheet may be attached to the barrier cuffs for example by gluing as illustrated by the dotted line at the distal edge 38, or any other bonding means known in the art. FIG. 5 shows another transversal cross-section close to the back edge 12 of the article, in the region where the back waist cap 63 is present, and where the absorbent core does not extend. As in the other cross-section views, horizontal dotted lines between two layers illustrate a possible adhesive bonding, while vertical dotted lines with a x show attachment bonding that can be made by fusion bonding or ultrasonic bonding, which for example allows attaching more than two layers in one bonding step, as is known in the art.

Figure 6:
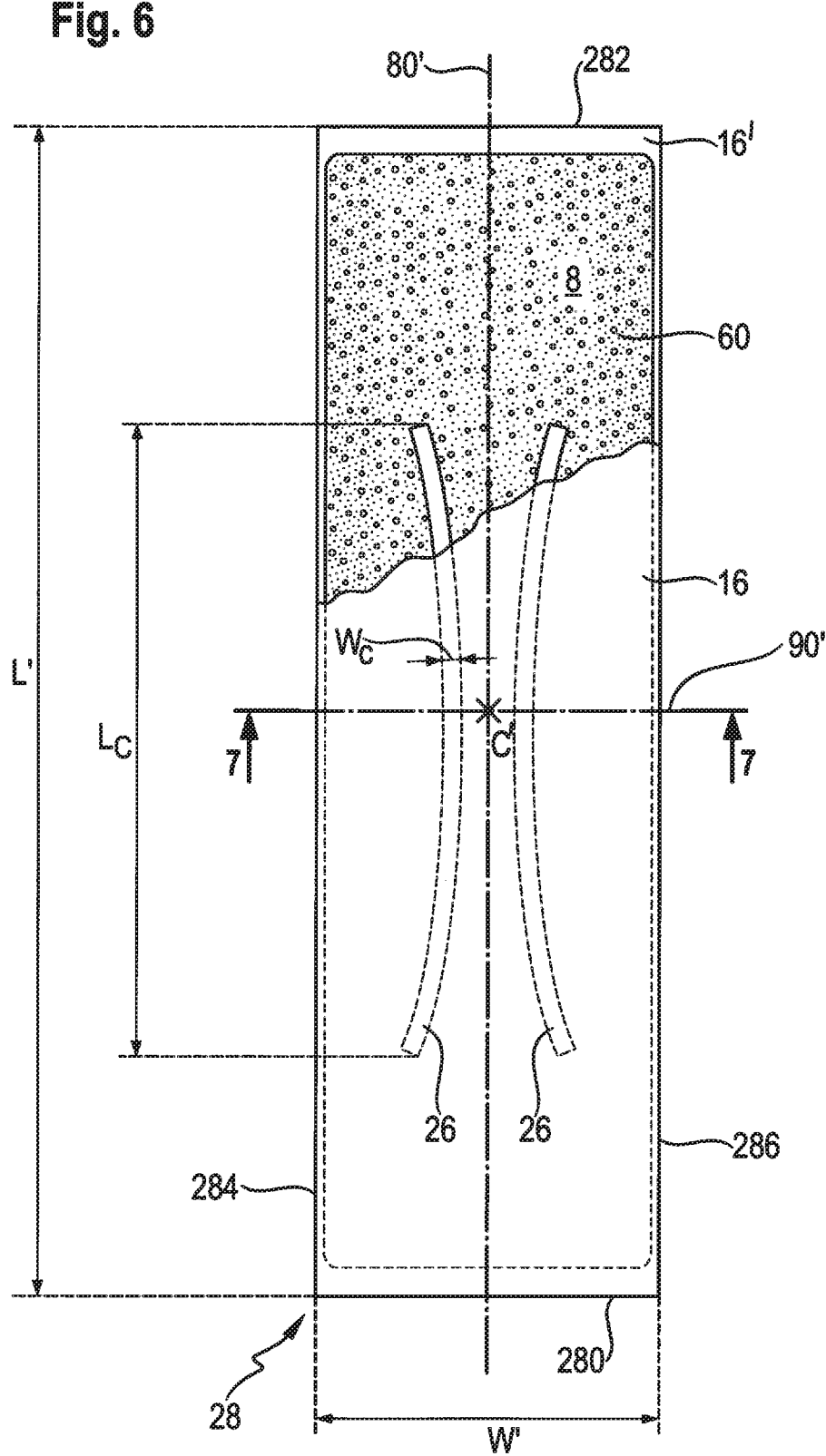
FIG. 6 shows an alternative absorbent core comprising longitudinally-extending channels.
Figure 7:
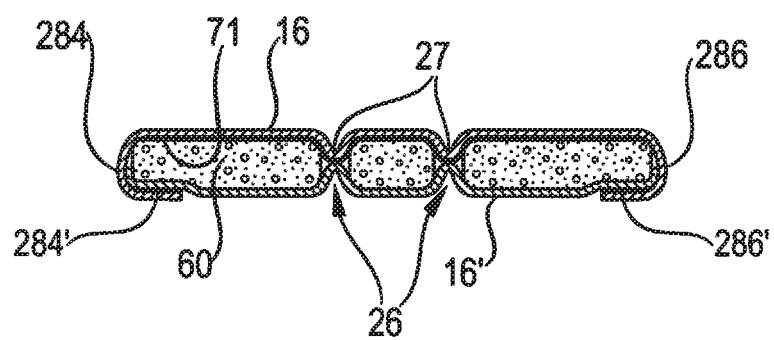
FIG. 7 shows a cross-section of the alternative absorbent core of FIG. 6.

The invention is not limited to particular components unless specified otherwise: any typical topsheet, backsheet or absorbent core may be used in the invention. The absorbent core may comprise one or more longitudinally-extending channel areas 26 to improve the flexibility and liquid distribution properties of the core. FIGS. 6 and 7 illustrate an exemplary absorbent core that may be optionally used in the present invention. The core comprises two longitudinally extending channel areas 26 that may be substantially free of absorbent material. This core will be discussed in further details in its individual section further below. The channel areas of the core may be substantially free of absorbent material and the top side of the core wrap may be optionally bonded to the bottom side of the core wrap through these channel areas to provide for channel bonds in dry and wet state. The absorbent core may however also comprise channel areas without core wrap bonds, or may be devoid of channels as shown in FIGS. 1-5. Likewise, a distribution layer 54 if present may also comprise one or more channels, in particular a pair of channels that may be free of distribution material. The channels in the distribution layer above the core may advantageously be at least partially superposed with the channel areas in the absorbent core, so that they at least partially match the shape and position of the channels.

The topsheet 24, the backsheet 25, the absorbent core 28, the waist caps 62, 63 and the other article components may be assembled in a variety of well-known configurations, in particular by gluing, fusion and/or pressure bonding. The absorbent article also comprises other typical diaper components which may or may not be represented in the Figures, such as a landing zone 44 on the front half of the diaper and serving as an attachment area for the fastening tabs 42 or an urine indicator disposed between the backsheet and the absorbent core that reacts by changing color when contacted with urine. These further components will be exemplified in more details further below. The absorbent article may also comprise other typical components, which are not represented in the Figures, such as a back elastic waist feature, a front elastic waist feature, transverse barrier cuffs, a lotion application, etc. . . .

Topsheet 24

The topsheet typically forms most of the wearer-contacting surface of the article and is typically the first layer that the body exudates contact. The topsheet is liquid permeable, permitting liquids to readily penetrate through its thickness. The topsheet is preferably compliant, soft-feeling, and non-irritating to the wearer's skin.

The topsheet of prior art commercial products are typically attached by gluing or otherwise to the rest of the article on their entire surface, and therefore are comprised in the same plane as the absorbent core, backsheet or gasketing cuffs. In contrast, in the present invention the topsheet comprises a raisable region 240 that is uncoupled from the chassis of the article underneath. The raisable region may be defined by a front side 241, a back side 242 and two longitudinally-extending sides 243, 244.

As represented in FIG. 4, the longitudinally-extending sides 243, 244 of the raisable portion of the topsheet are preferably attached at or close to the distal edges of the barrier leg cuffs where elastic strings 35 are present. This attachment to the barrier cuffs may be made by any conventional means such as adhesive bonding as represented by the dotted lines between the longitudinal sides of the topsheet and the distal edge 38 of the topsheet. The attachment may be as high as high possible on the barrier leg cuffs, up to the distal edge, but it is not excluded that the topsheet may be attached to the barrier leg cuffs at any intermediate position between the proximal edge 36 and the terminal edge 38.

The bottom layer 16' of the absorbent core is typically attached to the backsheet by a glue 125. The raisable portion 240 of the topsheet may be attached at its front side 241 and back side 242 to the backsheet (or another layer of the chassis) by the same adhesive 125 that serves to bond the bottom layer 16' of the absorbent core to the internal surface of the backsheet, as illustrated in FIG. 3. Typically, this adhesive application may take the form of a series of longitudinally extending glue slots or glue spirals. The adhesive is typically applied on the internal surface of the backsheet, and a portion of the adhesive may serve to form the gasketing cuffs 32. The glue pattern 125 may cover the entirety of the bottom layer 16' of the core wrap or more commonly only over a reduced portion of its surface, for example by application of a plurality of spiral glue pattern in selected areas as is exemplified in WO2012/170341 (Hippe et al.).

The front waist cap 62 and a back waist cap 63 may be further attached to the top surface of the topsheet adjacent the front and back edges of the article. The topsheet may be tucked between the waist caps and the backsheet at the front and back edges of the article. Since the waist caps are liquid impermeable this provides for protection from leakage at the front and back edges of the article. The waistcaps may be typically attached entirely by gluing or otherwise to the topsheet. The laminates formed by the waistcaps and the portions of the topsheet to which they are attached, may be only partially attached to the chassis towards the edge of the article as illustrated on FIG. 3. If the waistcaps are long enough to overlap with the absorbent core, the corresponding portion of the waist caps or of the topsheet-waistcaps laminate will not be attached to the chassis of the article. A partial attachment allows for the non-attached region of the topsheet-waistcaps laminate to be raised upwards with the rest of the raisable portion of the topsheet 240 relative to the rest of the article, thus providing for a sloped transition starting at the front side 241 and back side 242 of the raisable portion of the topsheet.

The present invention may be used with other conventional topsheets and suitable topsheets may be manufactured from a wide range of materials. Most topsheets are or comprise nonwoven materials or apertured formed films. Typical diaper topsheets have a basis weight of from about 10 gsm to about 28 gsm, in particular between from about 12 gsm to about 18 gsm, but higher basis weights are possible if it is desired to provide a very soft feeling wearer-contacting surface for example.

Any known topsheet may be used in the present invention, however the invention may be particularly useful when the topsheet comprises a plurality of apertures to ease penetration of exudates therethrough, such as urine and/or feces (solid, semi-solid, or liquid), as these exudates can be contained in the volume 300 under the uncoupled region of the topsheet and the rest of the article. Therefore, the topsheet may of the type comprising a plurality of apertures in the raisable region. At least some of the apertures may have an area ranging from 1 $mm^2$ to 20 $mm^2$, and the raisable region of the topsheet may in particular comprise on average from 1 to 20 apertures per $cm^2$. The aperture ratio (the surface of all the apertures divided by the overall surface of the topsheet in the raisable portion, measured when the topsheet is in a relaxed state, i.e. with just enough tension to smooth out any wrinkles) is advantageously in the range from 10% to 45%, in particular from 25% to 40%, more particularly from 30% to 35%. This range was found to provide enough passageways for the runny and liquid excrements into the empty volume 300 while minimizing potential re-wet, i.e. excrements flowing back in direction of the body.

The apertures may be formed in a nonwoven or in formed film as is known in the art. Apertured nonwovens are for example disclosed in U.S. Pat. No. 6,632,504 (Gillespie et al.). Apertured films may also be used as topsheet. Suitable formed film topsheets are for example described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643.

Nonwoven topsheets may be made of natural fibers (e.g., wood or cotton fibers), synthetic fibers or filaments (e.g. polyester or polypropylene or bicomponent PE/PP fibers or mixtures thereof), or a combination of natural and synthetic fibers. If the topsheet includes nonwoven fibers, the fibers may be spunbond, carded, wet-laid, meltblown, hydroentangled, or otherwise processed as is known in the art. In particular, the topsheet may be a spunbond PP nonwoven or a through-air bonded carded nonwoven web ("TABCW"). WO 2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

The topsheet may also have a three-dimensional appearance and feel, which is particularly useful to receive low viscous exudates such as the stool of young babies. Such three-dimensional layer may be formed from a single substrate such as a nonwoven layer or film which has been formed or treated accordingly. A three-dimensional layer may also be formed by combining two layers to form the desired three-dimensional surface. In a first example, an additional, smaller, three-dimensional layer may be placed on top of a conventional topsheet such as a nonwoven. This is additional layer is for example disclosed as fluid entangled dual layered three-dimensional materials in US 2014/0121623A1, US 2014/0121621A1, US2 014/0121624A1, US 2014/0121625A1.

The topsheet may also be a substrate formed from two layers, with a first layer comprising a hydrophobic material and second layer comprising a hydrophilic material with the first layer joined to the second layer, so that the substrate comprises a plurality of recesses, a plurality of projections, and a plurality of land areas, wherein the land areas surround at least a majority of the plurality of projections and a plurality of the recesses, wherein the plurality of recesses, the plurality of projections, and the plurality of land areas, together form a first three-dimensional surface on a first side of the substrate and a second three-dimensional surface on a second side of the substrate. This type of topsheet is disclosed in further details in WO 2015/134359 (Isele et al.) and US 2015/0250663A1 (Wagner et al.).

The topsheet may also comprise an acquisition layer wherein both layers are integrated with one other so that portion of one layer extend through the other layer, examples of such integrated topsheet having acquisition function, as well as apertured topsheets, are disclosed for example WO 2015/156952 (Arizti et al.).

The topsheet may be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US 2003/148684 and US2 005/008839 (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

Barrier Leg Cuffs 34 and Gasketing Cuffs 32

Absorbent articles such as taped diapers, diaper pants or adult incontinence pants typically comprise cuffs that improve the fit of the article around the legs of the wearer. Such cuffs typically comprise barrier leg cuffs 34 (also referred to as inner cuffs) and gasketing cuffs 32 (also referred to as outer cuffs). In the prior art, U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Both types of cuff may be partially formed by the same of piece of material 64, typically a nonwoven, which is one side partially bonded to the chassis and on the other side can be partially raised and thus stand up from the plane defined by the chassis, as shown for example in FIG. 4. The barrier leg cuffs 34, which comprise a raised portion of the material 64, provide improved containment of liquids and other body exudates approximately at the junction of the torso and legs of the wearer. The gasketing cuffs 32 which are formed in the plane of chassis also provide for improved containment in the crotch region of the wearer. Both types of cuffs may be advantageously elasticized, typically by elastic strings 33, 35.

The barrier leg cuffs 34 extend at least partially between the front edge and the back edge of the absorbent article on opposite sides of the longitudinal axis and are at least present adjacent to the center point C of the article. The cuff material may be made of any suitable material that has some barrier properties. Multilayer nonwoven comprising S and M layers, such as SMS, in particular of polypropylene are commonly used.

The barrier leg cuffs 34 are delimited by a proximal edge 36 joined to the rest of the article. The barrier leg cuffs 34 may be joined at the proximal edge 36 with the chassis of the article by adhesive bonding, fusion bonding, or any other known bonding means, for example as disclosed in WO 2014/168810A1 (Bianchi et al.). In typical diapers, the proximal edge may be joined to the topsheet, but in the present invention this may be the backsheet (as shown on FIG. 4) or another layer of the chassis. On the other end, a barrier leg cuff is delimited by a free terminal edge 38 that can be raised away from the chassis, and which is intended to contact and form a seal with the wearer's skin at the junction of the thighs and the crotch. Typically, the elastic strings 35 are comprised in a fold at the distal edges 38 which is adhesively maintained. Each barrier leg cuff 34 may comprise one, two or more elastic strings 35 close to its free terminal edge 38 to provide a better seal.

The barrier leg cuffs 34 of the present invention are attached to the longitudinal sides 243, 244 of the raisable region of the topsheet 24 at a position upwards from their proximal edge 36, in particular close to or at their distal edge 38. In this way, the raisable region 240 of the topsheet 24 is lifted up together with the barrier leg cuffs 34 when the article is worn by the user. An empty volume 300 is thus formed between the raisable region and the rest of the article underneath. This empty volume can store exudates either permanently for solid or semi-solid waste, or serve as a temporary buffer for urine until it is absorbent by the inner layers.

The barrier leg cuffs 34 are typically formed from a separate material 64 joined to the rest of the article, but it is not excluded that they may be formed by an extension of another layer, for example the backsheet. Typically, the material 64 of the barrier leg cuffs 34 may extend longitudinally along the whole length of the article, but is bonded flat towards the front edge and back edge of the article so that in these sections the barrier leg cuff material remains flush with the chassis of the diaper, as illustrated in FIG. 5. This bonding 164 may typically a fusion bonding that can bond several layers in one step, in the illustrated example the cuff material 64, the waist cap 63 and the topsheet 24.

The gasketing cuffs 32, which are in the same plane as the chassis of the absorbent article, are typically placed further laterally outwardly relative to the barrier leg cuffs 34. Typically, the barrier leg cuffs 34 are disposed more internally than the gasketing cuffs 32. The barrier leg cuffs are thus also referred to as inner cuffs and the gasketing cuffs as outer cuffs. The gasketing cuffs 32 can provide a better seal around the thighs of the wearer. Usually each gasketing leg cuff 32 will comprise one or more elastic string or elastic element 33 comprised in the chassis of the diaper for example between the cuff material 64 and the backsheet 25 in the area of the leg openings, as illustrated in the Figures. The articles of the invention preferably have gasketing cuffs 32 but this is not necessary.

Front Waist Cap 62 and Back Waist Cap 63

The absorbent articles of the invention advantageously comprise a front waist cap 62 or a back waist cap 63 and advantageously both a front waist cap and a back waist cap. The front and back waist caps extend inwardly from the front edge 10 and the back edge 12 of the article respectively and each have an inward-looking edge 621, 631. The waist caps are advantageously formed by a material having barrier properties such as a nonwoven made of synthetic fibers or a film and provide for barrier seals at the back and front edges 10, 12 of the article. The cuff material may be made of any suitable material that has some barrier properties. The same type of barrier material as disclosed for the barrier cuffs may be used for the waist caps. Multilayer nonwoven comprising S and M layers, such as SMS, in particular of polypropylene are commonly used as barrier material. The front and the back waist caps may be similarly constructed. If the term "waist caps" is used herein without further qualification, it refers to the front waist cap and/or the back waist cap, collectively and individually.

The waist caps advantageously extend longitudinally inwardly from the transversal edges of the articles and are at least partially attached to the topsheet. The front side 241 of the raisable region 240 of the topsheet is attached to the front waist cap 62 at a position intermediate the front edge of the article 10 and the inward-looking edge 621 of the front waist cap. Likewise, the back side 243 of the raisable region 240 of the topsheet is attached to the back waist cap 62 at a position intermediate the back edge 12 of the article and the inward-looking edge 631 of the back waist cap.

The waist caps are typically more elongated in the transversal direction than in the longitudinal direction. The waist caps may have a width which is at least 80%, or 100%, or 120% of the width of the topsheet, to provide for a good transversal seal at its junction with the topsheet. The waist caps may be generally rectangular. Advantageously, the inward-looking edges 621, 631 of the waistcaps are not straight but comprise a recess to minimize potential run-off of liquid excrements over the waist caps. The recess may have any shape but the inward-looking edges of the waist caps may be advantageously at least partially concavely curved in their middle. This is illustrated in FIG. 2. This recess minimize the overlap of the waist caps with the topsheet in the center of the diaper, where excrements are more likely to be released. The cuff material 64 may be joined laterally to the top of the waist caps 62, 63, for example by a fusion bonding 164, or an adhesive bonding if desired.

The outward-looking edge of each waist caps may be typically congruent with the back and front edges of the article respectively, which may also be curved as illustrated on FIG. 2. In particular the front edge 10 of the article may be concavely curved in its middle to provide for space for the umbilicus of new born babies. The back edge and front edge of the articles are typically formed simultaneously by cutting a continuous feed of not yet individualized articles, so that the front edge and the back edge of the articles match each other.

The waist caps 62, 63 may be disposed on top of the topsheet, to which they are bonded, for example by adhesive bonding. Other configurations are not excluded. For example the waist caps may be attached between the topsheet and the backsheet instead of above the topsheet. The front side 241 and the back side 242 of the raisable portion 240 of the topsheet are advantageously comprised in the region of the topsheet 24 attached to the waist caps 62, 63, as represented in FIG. 3. The waist caps may be thus partially attached (directly or indirectly) to the chassis (for example the backsheet as shown in the Figures) via the non-raisable portion of the topsheet on one side, and to the raisable portion of the topsheet on the other side. In this way, a portion of each waistcaps can be partially raised together with the raisable portion of the topsheet along the hinge-like lines corresponding to the front side and back side 241, 242 of the raisable portion of the topsheet, while the other portions of each waistcaps remain interdependent of the chassis. The waist caps provide for additional volume and barrier for temporarily storing body exudates towards the back and front edges of the articles, which may be particularly useful for example when the baby is respectively sleeping lying on his back or walking on all fours.

Acquisition Layer 52

The absorbent article may comprise an acquisition layer 52 disposed under the topsheet but not directly attached to the raisable portion 240 of the topsheet. An acquisition layer can quickly acquire the fluid away from the volume formed between the raised portion of the topsheet and the rest of the article. If a distribution layer 54 comprising loose fibers such as cellulose fibers is present, the acquisition layer 52 may also be used as a support for the fibers of the distribution layer during the manufacturing process.

The acquisition layer may typically be or comprise a non-woven material, for example a SMS or SMMS material, comprising a spunbonded, a melt-blown and a further spunbonded layer or alternatively a carded chemical-bonded nonwoven. The nonwoven material may be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). The acquisition layer may be stabilized by a latex binder, for example a styrene-butadiene latex binder (SB latex). Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US 2003/148684 (Cramer et al.) and US 2005/008839 (Cramer et al.). Processes for obtaining such latices are known, for example, from EP 149880 (Kwok) and US 2003/0105190 (Diehl et al.). The binder may typically be present in the acquisition layer in amount ranging from about 12% to about 50%, for example about 30%, by total weight of the acquisition layer. SB latex is available under the trade name GENFLO™ 3160 (OMNOVA Solutions Inc.; Akron, Ohio).

Another typical acquisition layer, sometimes referred to as secondary topsheet, may for example be a through-air bonded carded web ("TABCW") but many other alternatives material are known in the art and may be used instead. "Bonded carded web" refers to webs that are made from staple fibers that are sent through a combing or carding unit, which breaks apart and aligns the staple fibers in the machine direction to form a generally machine direction-oriented fibrous nonwoven web. This web is then drawn through a heated drum, creating bonds throughout the fabric without applying specific pressure (thru air bonding process). The TABCW material provides a low density, lofty through-air bonded carded web. The web may for example have a specific weight basis level at about 15 gsm to about 120 gsm (gram per m2), in particular about 30 gsm to about 80 gsm. The TABCW material can for example comprise about 3 to about 10 denier staple fibers. Examples of such TABCW are disclosed in WO 2000/71067 (KIM DOO-HONG et al.). TABCW are available directly from all usual suppliers of nonwoven webs for use in absorbent articles, for example Fitesa Ltd or Fiberweb Technical Nonwovens.

A further acquisition layer (not shown) may be used in addition to the first acquisition layer described above. For example, a tissue layer may be placed between the first acquisition layer and the distribution layer. The tissue may have enhanced capillarity distribution properties compared to the acquisition layers described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

Distribution Layer 54

The absorbent article may comprise a distribution layer 54 between the topsheet 24 the absorbent core 28, more particularly between the acquisition layer 52 and the absorbent core 28 if an acquisition layer is present. The distribution layer can spread an insulting fluid liquid over a larger surface within the article so that the absorbent capacity of the core can be more efficiently used. Typically, distribution layers are made of a fibrous material based on synthetic or cellulosic fibers and has a relatively low density. The density of the distribution layer where the fibrous material is present may vary depending on the compression of the article, but may typically range from 0.03 $g/cm^3$ to 0.25 $g/cm^3$, in particular from 0.05 $g/cm^3$ to 0.15 $g/cm^3$, measured at 0.30 psi (2.07 kPa), and may be for example measured at the centerpoint C of the article.

An exemplary distribution material comprises or consists of cross-linked cellulose fibers but other typical distribution materials can also be used. The cross-linked cellulosic fibers may be crimped, twisted, or curled, or a combination thereof including crimped, twisted, and curled. This type of material has been used in the past in disposable diapers as part of an acquisition system, for example US 2008/312622 A1 (Hundorf et al.). The cross-linked cellulosic fibers provide higher resilience and therefore higher resistance against the compression in the product packaging or in use conditions, e.g. under baby weight. Exemplary chemically cross-linked cellulosic fibers suitable for a distribution layer are disclosed in U.S. Pat. Nos. 5,549,791, 5,137,537, WO 95/34329 or US 2007/0118087. Exemplary cross-linking agents include polycarboxylic acids such as citric acid and/or polyacrylic acids such as acrylic acid and maleic acid copolymers. For example, the cross-linked cellulosic fibers may have between about 0.5 mole % and about 10.0 mole % of a C2-C9 polycarboxylic acid cross-linking agent, calculated on a cellulose anhydroglucose molar basis, reacted with said fibers in an intrafiber ester crosslink bond form.

The distribution layer may be rectangular or otherwise shaped, for example the distribution layer may be bullet-shaped with the rounded edge is oriented towards the back of the article as illustrated in FIG. 2. The distribution layer may be profiled so that the basis weight (amount of material per unit of surface) varies in the areas of the distribution layer comprising the fibrous material. The layer may be longitudinally and/or transversally profiled, with typically higher basis weight towards the front and the middle of distribution layer relative to the back and sides of the distribution layer. This is further discussed in WO 2014/93323A1 (Bianchi et al.). The distribution (or acquisition) layer may also comprise channels which are areas substantially free of distribution (or acquisition) material and may at least partially correspond to the channel areas 26 in the absorbent core 28, if these are present. See for example WO 2015/31225A1 (Roe et al.) for further example of a distribution layer with channels. These secondary channels can have different width as the core's channels but advantageously follow the outline of the absorbent core channels 26 along at least a portion of their length, for example at least 50% and up to 100% of their length.

Absorbent Core 28

The absorbent article 20 comprises an absorbent core 28 which comprises an absorbent material 60 for acquiring and storing fluid. The absorbent cores of the invention may be any conventional absorbent cores known in the art and typically comprises an absorbent material contained in a core wrap. As used herein, the term "absorbent core" does not include the topsheet, the backsheet, the distribution layer and the acquisition layer. The absorbent core has the most absorbent capacity of all the components of the absorbent article, and comprises all or at least most of the superabsorbent polymer (SAP) in the article. The core typically may thus consist essentially of, or consists of, the core wrap, the absorbent material, and optionally adhesives. The absorbent material may consist of SAP in particulate form as exemplified in the present description but it is not excluded that other type of absorbent material may be used. The terms "absorbent core" and "core" are herein used interchangeably.

The absorbent material in the core may comprise fibers mixed with superabsorbent polymers (herein abbreviated as "SAP" also referred to as absorbent gelling material, further exemplified below). The fibers may typically comprise wood pulp (cellulose) fibers optionally mixed with synthetic fibers. The absorbent material typically comprises from 50% to 90% of SAP by weight of the absorbent material. The absorbent material may for example comprise at least 55% superabsorbent polymers by weight of the absorbent material, in particular from 60% to 90% superabsorbent polymers by weight of the absorbent material, in particular from 65% to 85% superabsorbent polymers by weight of the absorbent material.

It however not excluded that higher amount of SAP may be present, on the contrary the absorbent material may also comprise little or no cellulose fibers (so called airfelt-free cores). The absorbent articles may thus also have a core consisting essentially of SAP without cellulose fibers as absorbent material. For example, WO 2008/155699 (Hundorf et al.) discloses absorbent cores with a patterned layer of SAP immobilized by a net of fibrous thermoplastic adhesive material deposited over the layer of SAP. The fibrous thermoplastic material helps maintaining the SAP in position within the absorbent core prior to and during use of the article, without substantially restricting the ability of the SAP to absorb large volumes of urine.

An exemplary absorbent core 28 is represented in isolation on FIGS. 6-7. The absorbent core can notionally (i.e. virtually) comprise a longitudinal axis 80' extending from the front edge 280 to the back edge 282 and dividing the core in two substantially symmetrical halves relative to this axis, when viewing the core in the plane formed by the longitudinal and transversal direction. The longitudinal axis 80' of the core may be generally parallel and superposed with the longitudinal axis 80 of the absorbent article 20. The absorbent core can typically be generally rectangular including the region of the core wrap which does not enclose the absorbent material, in particular at the front and back end seals when present. In case the core is not rectangular, the maximum dimension measured along the transversal direction and the longitudinal direction can be used to report the width W' and length L' of the core respectively. The width and length of the core may vary depending on the intended usage. For baby and infant diapers, the width of the core may for example in the range from 40 mm to 200 mm and the length of the core from 100 mm to 600 mm. Adult incontinence products may have higher maximum dimensions.

The absorbent material is present within a deposition area 8 defined by the periphery of the layer of absorbent material 60 within the core wrap, as seen from the top side of the absorbent core. The absorbent material deposition area 8 can take various shapes, such as rectangular (as represented), "dog bone" or "hour-glass" shape, which shows a tapering along its width towards the middle or "crotch" region of the core. In this way, the absorbent material deposition area may have a relatively narrow width in an area of the core intended to be placed in the crotch region of the absorbent article.

The basis weight (amount deposited per unit of surface) of the SAP may also be varied along the deposition area 8 to create a profiled distribution of absorbent material, in particular SAP, in the longitudinal direction, in the transversal direction, or both directions of the core. Hence along the longitudinal axis of the core, the basis weight of absorbent material may vary, as well as along the transversal axis, or any axis parallel to any of these axes. The basis weight of SAP in area of relatively high basis weight may thus be for example at least 10%, or 20%, or 30%, or 40%, or 50% higher than in an area of relatively low basis weight. In particular the SAP present in the absorbent material deposition area at the level of the centerpoint point C may have more SAP per unit of surface deposited as compared to another area of the absorbent material deposition area.

Core Wrap 16, 16'

The absorbent core typically comprises a core wrap which encloses the absorbent material. Various core wrap constructions are possible. The core wrap may for example comprise two separate substrates forming the top side 16 and the bottom side 16' of the core wrap respectively. The two substrates may be attached in a C-wrap configuration with one of the substrate larger than the other so that it can form two flaps that are folded back on the other substrate, the flaps are then bonded by two longitudinal seals 284', 286' along its longitudinal edges 284, 286, as represented in FIG. 7. The core wrap may also comprise two substrates disposed flat in a face to face relation (sandwich) without fold over along the longitudinal sides 284, 286. The core wrap may also optionally comprise a front edge seal and a back edge seal (not represented). However this core wrap construction is not limiting of the invention, as any conventional core wrap construction may also be used, for example a single substrate on a portion of which the absorbent material is deposited to form the first side and then the rest of the substrate folded over the deposited absorbent material to form the other side of the core wrap. This single substrate construction can then be sealed longitudinally with a single longitudinal edge seal.

The substrates may be formed by any materials suitable for receiving and containing the absorbent material. Typical substrate materials used in the production of conventional cores may be used, in particular paper, tissues, films, wovens or nonwovens, or laminate of any of these. As used herein, the terms "nonwoven layer" or "nonwoven web" generally means an engineered fibrous assembly which has been given a designed level of structural integrity by physical and/or chemical means with the exclusion of paper, woven or knitted materials. The fibers may be of natural or synthetic origin and may be staple or continuous filaments or be formed in situ. Nonwoven webs can be formed by many processes such as meltblowing, spunbonding, solvent spinning, electrospinning, carding and airlaying. The basis weight of nonwoven webs is usually expressed in grams per square meter (g/m2 or gsm). Nonwoven materials are typically made of synthetic fibers, such as PE, PET and in particular PP fibers.

The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932A1, US 2011/0319848A1 and US 2011/0250413A1. It is also possible than the core wrap may be at least partially formed from a component of the article having another function than substrate for the absorbent material. For example, it is possible that the backsheet may form the bottom side of the core wrap and/or that a distribution layer or the topsheet may form the top side of the core wrap. However, typically the core wrap is made of one or more substrates whose only function is to receive and enclose the absorbent material, as indicated previously.

Channel Areas 26 in the Absorbent Core

The absorbent core 28 comprises in one aspect of the invention at least one and advantageously at least two longitudinally-extending channel areas 26 (referred hereinafter in the plural form). By "substantially free" it is meant that they do not comprise absorbent material except possibly for minimal amount such as involuntary contaminations with absorbent material particles that may occur during the core making process. The top side 16 of the core wrap may be attached to the bottom side 16' of the core wrap by core wrap bonds 27 through these areas substantially free of absorbent material. The channel areas 26 are advantageously surrounded by absorbent material 60 within the deposition area 8. When the absorbent material swells upon absorbing a liquid, the core wrap bonds 27 remain at least initially attached in the channel areas 26. The absorbent material 60 swells in the rest of the core when it absorbs a liquid, so that the core wrap forms one or more visible channels along the channel areas 26 comprising the core wrap bond. These channels are three dimensional and provide axes of flexibility that can help forming the empty volume between the topsheet and the chassis of the article. Furthermore they can serve to distribute an insulting fluid along their length to a wider area of the core. They may provide a quicker fluid acquisition speed and a better utilization of the absorbent capacity of the core. It is not excluded that the channel areas may be without a core wrap bond, as this may be easier to manufacture, but these non-bonded areas will typically not form permanent three-dimensional channels when wet.

The top side 16 and the bottom side 16' of the core wrap may be bonded together continuously along the channel areas 26, but the core wrap bond 27 may also be discontinuous (intermittent) such as formed by series of point bonds. An auxiliary glue 71 may be used to at least partially form the substrates bond 27. In this case, some pressure may be applied on the substrates in the zones 26 to improve the adhesive bonds between the substrates. If an optional fibrous adhesive is present, it may also help forming the bond 27. If the auxiliary glue is applied as a series of longitudinally orientated continuous slots, the width and frequency of these slots may advantageously be such that at least one slot of auxiliary glue is present at any level of the channel area 26 in the longitudinal direction. For example, the slots may be 1 mm wide with a 1 mm distance between each slots, and the channel areas have a width of about 8 mm. Such on average for 4 slots of auxiliary glue will be present in each of the channel area 26. It is of course also possible to form the bonds 27 via other known attachment means, such as pressure bonding, ultrasonic bonding, heat bonding or combination thereof.

The channel areas 26 extend substantially longitudinally, meaning that each areas extends at least as much in the longitudinal direction than in the transversal direction, and typically at least twice as much in the longitudinal direction than in the transverse direction (as measured after projection on the respective axis). The channel areas 26 may have a length Lc projected on the longitudinal axis 80 of the core that is at least 20% of the length L' of the absorbent core, in particular from 25%, or from 30% to 90% of the length L' of the core. The channel areas may have a width Wc along at least part of their length which is at least 2 mm, or at least 3 mm or at least 4 mm, up to for example 20 mm, or 16 mm or 12 mm. The width of each channel areas substantially free of absorbent material may be constant through substantially its whole length or may vary along its length.

The channel areas may be typically at least partially curved. In particular the channel areas present in the crotch region may be concave towards the longitudinal axis 80 as illustrated in the Figure. Alternatively, it is not excluded that the channel areas may be partially or entirely straight, and in particular longitudinally oriented parallel to the longitudinal axis 80, or curved in the other direction. The channel areas are typically disposed as one or more symmetrical pair(s) relative to the longitudinal axis, and are spaced apart from one another over their whole longitudinal dimension.

These channel areas in the core may at least be partially superposed with channels in a distribution or acquisition layer, if present. In this way, the fluid can be directly transferred vertically first via the channels in the distribution layer to the channel areas of the absorbent core, where it can be spread longitudinally along the length of the channels. The absorbent core may also comprise a rear pocket that may be at least partially superposed with the back pocket of the distribution layer. Typically the absorbent core is longer and wider than the distribution layer. Exemplary absorbent cores comprising channel areas and back pockets are disclosed for example in WO 2014/093129A1 (Roe et al.).

The absorbent core may have a profiled distribution of absorbent material in the longitudinal direction, especially having a higher basis weight in the front half of the article than in the back half of the article. The absorbent core may also be profiled in the transversal direction, in particular, the absorbent core and the distribution layer may be similarly profiled in the transversal direction. Thus, the average basis weight of the absorbent material in the central absorbent zone between the channels of the core may be higher or lower than the average basis weight of absorbent material in the whole of the core (excluding the channels if these are material free). The average basis weight of the absorbent material in the central absorbent zone may differ by at least 10% than the average basis weight, in particular by at least 25%, or by at least 50%, or by at least 100%.

Absorbent Material 60

The absorbent material may be any known absorbent material known in the art, but will typically comprise or consist of superabsorbent polymers (herein referred to as "SAP"). The SAP may be typically in particulate forms (superabsorbent polymer particles), optionally mixed with cellulose fibers, but it not excluded that other forms of SAP may be used such as a superabsorbent polymer foam for example. The SAP useful in the present invention includes a variety of water-insoluble, but water-swellable polymers capable of absorbing large quantities of fluids. The term "superabsorbent polymer" refers herein to absorbent materials, which may be cross-linked polymeric materials, that can typically absorb at least 10 times their weight of an aqueous 0.9% saline solution as measured using the Centrifuge Retention Capacity (CRC) test (EDANA method WSP 241.2.R3 (12). The SAP may in particular have a CRC value of more than 20 g/g, or more than 24 g/g, or of from 20 to 50 g/g, or from 20 to 40 g/g, or 24 to 30 g/g.

The superabsorbent polymers may be in particulate form to be flowable in the dry state and thus easily deposited on a substrate. Typical particulate absorbent polymer materials are made of poly(meth)acrylic acid polymers. However, starch-based particulate absorbent polymer materials may also be used, as well polyacrylamide copolymer, ethylene maleic anhydride copolymer, cross-linked carboxymethyl-cellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in WO 07/047598, WO 07/046052, WO 2009/155265 and WO 2009/155264. Suitable superabsorbent polymer particles may be obtained by current state of the art production processes, for example as described in WO 2006/083584. The superabsorbent polymers are preferably internally cross-linked, i.e. the polymerization is carried out in the presence of compounds having two or more polymerizable groups which can be free-radically copolymerized into the polymer network.

The absorbent core typically comprises only one type of SAP, but it is not excluded that a blend of different SAPs may be used. The fluid permeability of a superabsorbent polymer can be quantified using its Urine Permeability Measurement (UPM) value, as measured in the test disclosed in US patent application number US 2014/005622A1. The UPM of the SAP may for example be of at least $10 \times 10^{-7}$ $cm^3 \cdot sec/g$, or at least $30 \times 10^{-7}$ $cm^3 \cdot sec/g$, or at least $50 \times 10^{-7}$ $cm^3 \cdot sec/g$, or more, e.g. at least 80 or $100 \times 10^{-7}$ $cm^3 \cdot sec/g$. The SAP particles may have a time to reach an uptake of 20 g/g (T20) of less than 240 s, preferably from 40 s to less than 240 s, more preferably from 65 s to 215 s, as measured according to the K(t) test method as described in WO 2015/041784 (Peri et al).

The total amount of absorbent material should be sufficient for the application considered. For baby diapers for example, the amount of superabsorbent material (SAP) should be sufficient to provide overnight dryness. For children having a weight range of 8-17 kg, as an example, the total amount of SAP in the core may range from about 8 g to 12 g or more. The present invention is especially useful for smaller size diapers for new babies, and in these cases the overall amount of SAP in the article may for example range from about 2 g to about 10 g, in particular from about 3 g to about 8 g of SAP.

The absorbent material may be deposited using known techniques, which may allow relatively precise deposition of SAP at relatively high speed. In particular the SAP printing technology as disclosed for example in US 2006/24433 (Blessing), US 2008/0312617 and US 2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate. The channels of the absorbent core can be formed for example by modifying the pattern of the grid and receiving drums so that no SAP is applied in certain areas to form absorbent material free areas in the form of channels. EP 2,532,329 (Jackels et al.) discloses this modification in more details.

Fastening System 42, 44

The absorbent article may include a fastening system, especially when the article is a taped diaper as exemplified in FIG. 1. The fastening system can be used to provide lateral tensions about the circumference of the absorbent article to hold the absorbent article on the wearer. Such a fastening system is not necessary for pant articles such as training pants and adult incontinence pants since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,86, and 5,591,152.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of less than 0.1 mm. The basis weight of those films is usually as low as possible to save material costs, typically from 10 gsm to 30 gsm, in particular below 20 gsm. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films. The film may include at least about 20 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

The backsheet may further typically comprise a nonwoven on its most external side to improve softness. Exemplary laminates comprising a breathable film and a nonwoven layer are for example disclosed in WO 2014/022362A1, WO 2014/022652A1 and U.S. Pat. No. 5,837,352. The nonwoven web may in particular comprise a spunbond nonwoven web and/or a laminate of a spunbond nonwoven web and a meltblown nonwoven web. The laminate may also have a water vapor transmission rate of at least 300 g/m2/24 hours. U.S. Pat. No. 5,843,056 for example discloses substantially liquid impermeable, vapor permeable composite backsheet.

Front and Back Ears 46, 40

The absorbent article may comprise front ears 46 and back ears 40 as is known in the art in taped diapers. Training pants which are already sealed along the waist edges typically do not require front ears and back ears. The ears can be integral part of the chassis, for example formed from the topsheet and/or backsheet as side panel. Alternatively, as represented in FIG. 1, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Other Components

The absorbent articles of the invention can further comprise any other typical components known for the intended purpose of the article which may or may not be illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO 2014/093310 where several examples of these components are disclosed in more details.

The absorbent article may also comprise at least one elastic waist band (also called elastic waist feature) disposed parallel to and along the back edge of the article. The articles may also comprise such an elastic waist feature parallel to and along the front edge of the article. Such waistbands help providing improved fit and containment at the back and/or front edge of the article. The elastic waist feature is generally intended to elastically expand and contract to dynamically fit the wearer's waist. The elastic waist feature may be constructed in different configurations. Non-limiting examples of back and front waistbands can be found in WO 2012/177400 and WO 2012/177401 (Lawson), and U.S. Pat. Nos. 4,515,595, 4,710,189, 5,221,274 and 6,336,922 (VanGompel et al.).

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is represented in the Figures by horizontal dotted lines for adhesive bonding and vertical dotted lines for fusion bonding. Adhesives may be typically used to improve the adhesion of the different layers, for example between the backsheet and the core wrap. The adhesives used may be any standard hotmelt glue as known in the art. The individual layers of the articles may of course be converted into an absorbent article according to any of the processes known in the art, unless otherwise indicated.

Packages

A plurality of articles according to the invention may be packaged in a package for transport and sale. At least 50% of the articles in the package may be according to the invention, and preferably substantially all the articles. The articles may be folded and packaged according to any conventional packages is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression may be typically sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 75 mm to 110 mm, from 80 mm to 110 mm, from 80 mm to 105 mm, or from 80 mm to 100 mm, specifically reciting all 0.1 mm increments within the specified ranges and all ranges formed therein or thereby, according to the In-Back Stack Height Test described herein.

In-Bag Stack Height Test

The In-Bag Stack Height (IBSH) of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure: Absorbent article packages are equilibrated at 23±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Miscellaneous

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An absorbent article for personal hygiene having a front edge and a back edge notionally defining a longitudinal axis extending from the middle of the front edge to the middle of the back edge, the absorbent article comprising:
   a garment-facing side comprising a liquid impermeable backsheet;
   a wearer-facing side comprising a liquid permeable topsheet;
   an absorbent core between the topsheet and the backsheet, the absorbent core comprising an absorbent material;
   a chassis comprising the absorbent backsheet and the absorbent core;
   a pair of elasticized barrier leg cuffs, each barrier leg cuff defined by a proximal edge attached to the chassis of the article and a terminal edge that can be raised away from the chassis; wherein the topsheet comprises a raisable region attached to the barrier leg cuffs at a position away from the proximal edges of the barrier leg cuffs, so that when the barrier leg cuffs are raised away from the chassis, the raisable region is lifted up by the barrier leg cuffs and an empty volume is formed between the raisable region and the chassis and the raisable region is defined by a front side, a back side and two longitudinally-extending sides, wherein the longitudinally-extending sides are at least partially attached to the barrier leg cuffs and the front side and the back side are at least partially attached to the chassis; and
   a front waist cap adjacent the front edge of the article;
   a back waist cap adjacent the back edge of the article;
      wherein the front side and back side of the raisable region are respectively attached to the front waist cap and the back waist cap so that the front waist cap and the back waist cap are at least partially raised simultaneously with the raisable region of the topsheet; and
   wherein the length of the wearer-facing side of the article is shorter than the length of the garment-facing side of the article, as measured along the longitudinal axis.

2. An absorbent article according to claim 1, wherein the topsheet comprises a plurality of apertures in the raisable region.

3. An absorbent article according to claim 2, wherein at least some of the plurality of apertures have an area ranging from about 1 mm² to about 20 mm², and the raisable region comprises on average from about 1 to about 20 apertures per cm².

4. An absorbent article according to claim 2, wherein the aperture ratio of the topsheet in its raisable portion ranges from about 10% to about 40%.

5. An absorbent article according to claim 1, wherein the topsheet comprises three-dimensional features that protrudes from the wearer-facing surface of the topsheet.

6. An absorbent article according to claim 1, further comprising an acquisition layer between the topsheet and the absorbent core, and wherein the raisable region of the topsheet is not attached to the acquisition layer.

7. An absorbent article according to claim 1, wherein the absorbent core comprises at least a pair of longitudinally-extending channel areas which are substantially free of absorbent material.

8. An absorbent article according to claim 7, wherein the absorbent core comprises a core wrap having a top side and a bottom side enclosing the absorbent material, and wherein the top layer and the bottom layer of the absorbent core are attached through the channel areas.

9. An absorbent article according to claim 7, wherein the channel areas have length as measured in the direction of the longitudinal axis which is at least about 20% of the length of the absorbent core as measured projected on the longitudinal axis.

10. An absorbent article according to claim 1, wherein the front edge of the article comprises a recess at its middle.

11. An absorbent article for personal hygiene having a front edge and a back edge notionally defining a longitudinal axis extending from the middle of the front edge to the middle of the back edge, the absorbent article comprising:
 a garment-facing side comprising a liquid impermeable backsheet;
 a wearer-facing side comprising a liquid permeable topsheet;
 an absorbent core between the topsheet and the backsheet, the absorbent core comprising an absorbent material;
 a chassis comprising the absorbent backsheet and the absorbent core;
 a pair of barrier leg cuffs disposed symmetrically relative to the longitudinal axis, each barrier leg cuff defined by a proximal edge attached to the chassis of the article and an elasticized terminal edge that can be raised away from the chassis;
 wherein the topsheet comprises a raisable region defined by a front side, a back side and two longitudinally-extending sides, wherein the longitudinally-extending sides are at least partially attached to the barrier leg cuffs at a position away from the proximal edges of the barrier leg cuffs, and the font side and back side are at least partially attached to the chassis; so that when the barrier leg cuffs are raised away from the chassis, the raisable region of the topsheet is lifted up by the barrier leg cuffs and an empty volume is formed between the raisable region and the chassis;
  a front waist cap extending inwardly from the front edge of the article and having an inward-looking edge, wherein the front side of the raisable region of the topsheet is attached to the front waist cap at a position intermediate the front edge of the article and the inward-looking edge of the front waist cap; and/or
  a back waist cap extending inwardly from the back edge of the article and having an inward-looking edge, wherein the back side of the raisable region of the topsheet is attached to the back waist cap at a position intermediate the back edge of the article and the inward-looking edge of the back waist cap,
 so that a portion of one selected from the front waist cap, the back waist cap or both, are raised simultaneously with the raisable region of the topsheet; and
 wherein the inward-looking edge of one selected from the front waist cap, the back waist cap or both, comprises a recess.

12. An absorbent article according to claim 11, wherein the absorbent core comprises one or more longitudinally-extending channel areas which are substantially free of absorbent material.

13. An absorbent article according to claim 12, wherein the absorbent core comprises a core wrap having a top side and a bottom side enclosing the absorbent material, and wherein the top layer and the bottom layer of the absorbent core are attached through the one or more channel areas.

14. An absorbent article according to claim 11, wherein the length of the wearer-facing side of the article is shorter than the length of the garment-facing side of the article, as measured along the longitudinal axis.

\* \* \* \* \*